United States Patent [19]

Watts et al.

[11] Patent Number: 5,013,150

[45] Date of Patent: * May 7, 1991

[54] METHOD FOR DETECTION OF FLUORESCENCE OR LIGHT SCATTER

[75] Inventors: Richard P. Watts, San Mateo; Wylie I. Lee, Laguna Beach; John W. Vorpahl, Livermore, all of Calif.

[73] Assignee: Syntex (U.S.A.) Inc., Palo Alto, Calif.

[ * ] Notice: The portion of the term of this patent subsequent to Jun. 19, 2007 has been disclaimed.

[21] Appl. No.: 498,065

[22] Filed: Mar. 23, 1990

Related U.S. Application Data

[63] Continuation of Ser. No. 176,475, Apr. 1, 1988, Pat. No. 4,934,811.

[51] Int. Cl.[5] .................... G01N 21/49; G01N 21/64
[52] U.S. Cl. .................... 356/73; 250/227.11; 356/318; 356/336; 356/338
[58] Field of Search ............... 356/73, 336, 338, 318; 250/227.11

[56] References Cited

U.S. PATENT DOCUMENTS

| | | | |
|---|---|---|---|
| 3,941,485 | 3/1976 | Madden | 356/429 X |
| 4,071,298 | 1/1978 | Falconer | 356/336 X |
| 4,421,860 | 12/1983 | Elings et al. | 436/518 |
| 4,529,306 | 7/1985 | Kilham et al. | 356/338 X |
| 4,537,861 | 8/1985 | Elings et al. | 436/518 |
| 4,560,881 | 12/1985 | Briggs | 250/458.1 |
| 4,564,598 | 1/1986 | Briggs | 436/501 |
| 4,643,573 | 2/1987 | McLachlan et al. | 356/338 |
| 4,676,640 | 6/1987 | Briggs | 356/317 |
| 4,707,134 | 11/1987 | McLachlan et al. | 250/574 X |
| 4,753,530 | 6/1988 | Knight et al. | 356/318 X |

FOREIGN PATENT DOCUMENTS 1506017 4/1978 United Kingdom .

OTHER PUBLICATIONS

Abstract of Japanese Patent Appln 84230306, 5/1986.
PCT Patent Appln. Publication No. WO85/05680 Published Dec. 19, 1985.

*Primary Examiner*—Vincent P. McGraw
*Attorney, Agent, or Firm*—John A. Dhuey

[57] ABSTRACT

An apparatus and method are described for defining a small interrogation volume in a liquid sample suspected of containing an analyte. The apparatus and method utilize a dual optical fiber probe constructed with the ends of the optical fibers at the liquid-fiber interface spatially oriented such that the intersection of their longitudinal axes forms an included angle ranging from about 40° to 140°. By appropriate choice of the numerical aperture and core diameter of the optical fibers and the separation distance between the longitudinal axes of the optical fibers at the liquid-fiber interface, a finite interrogation volume of predetermined size and independent of the total liquid sample volume can be defined. The apparatus and method substantially reduce background interference with corresponding increase in assay sensitivity.

1 Claim, 3 Drawing Sheets

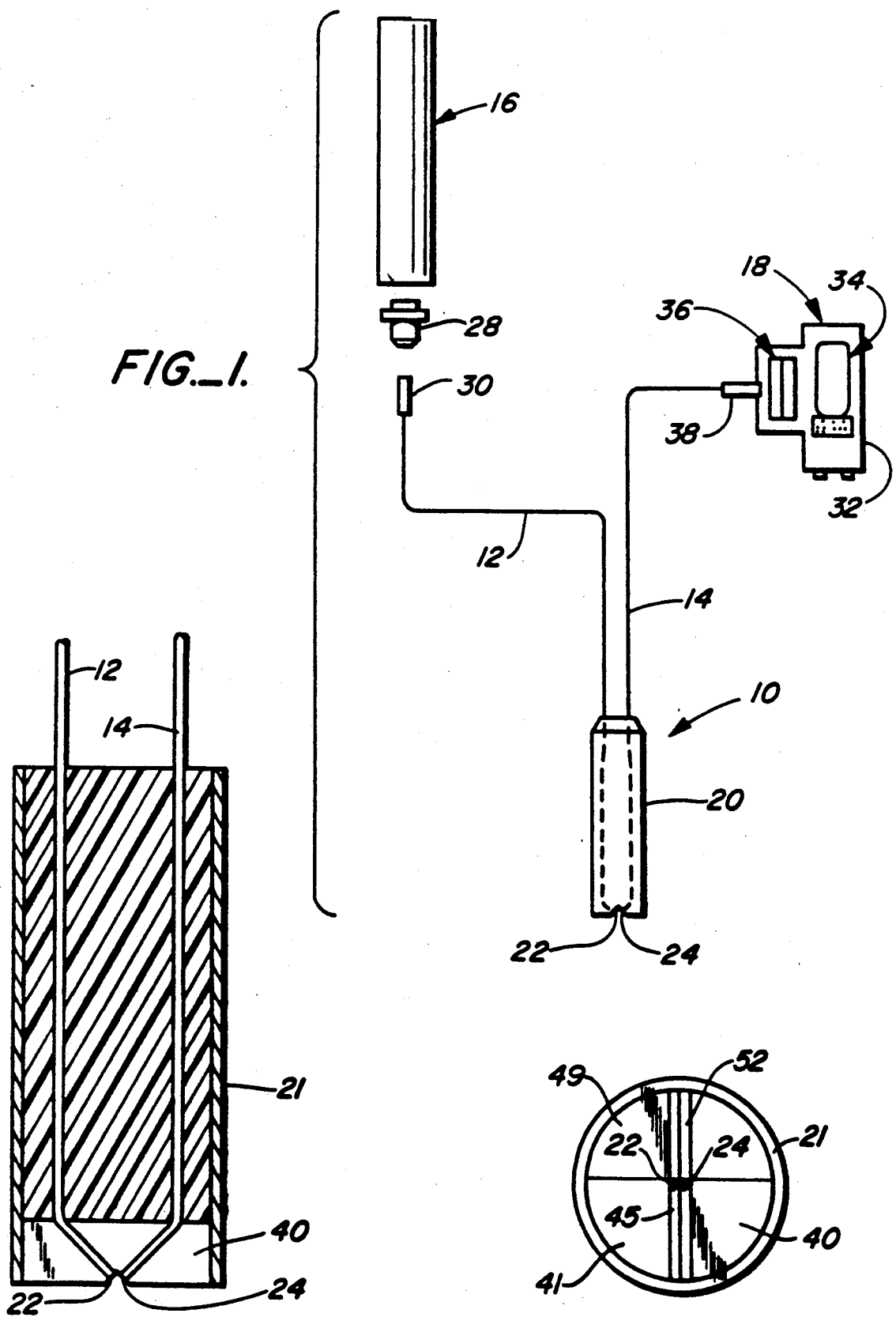
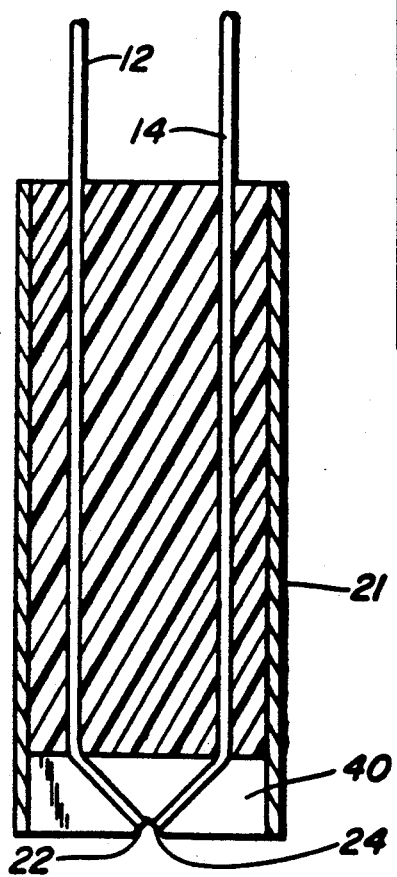
FIG._2.
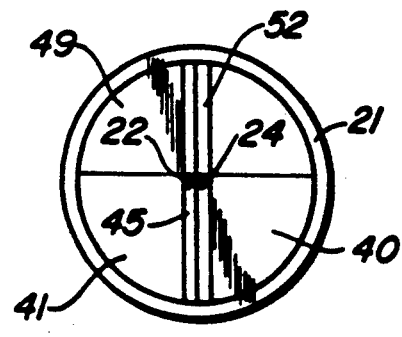
FIG._3.

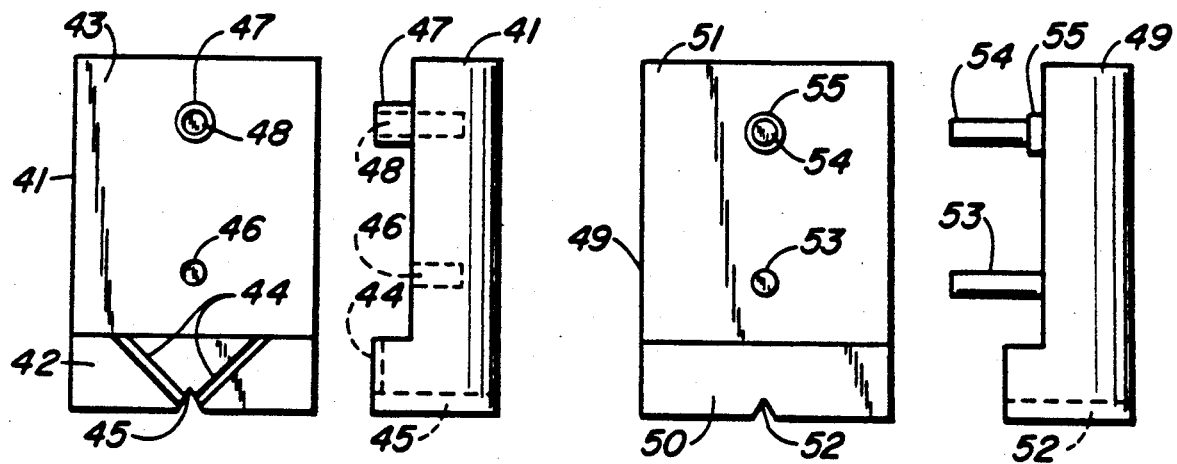
FIG._4A.  FIG._4B.  FIG._5A.  FIG._5B.
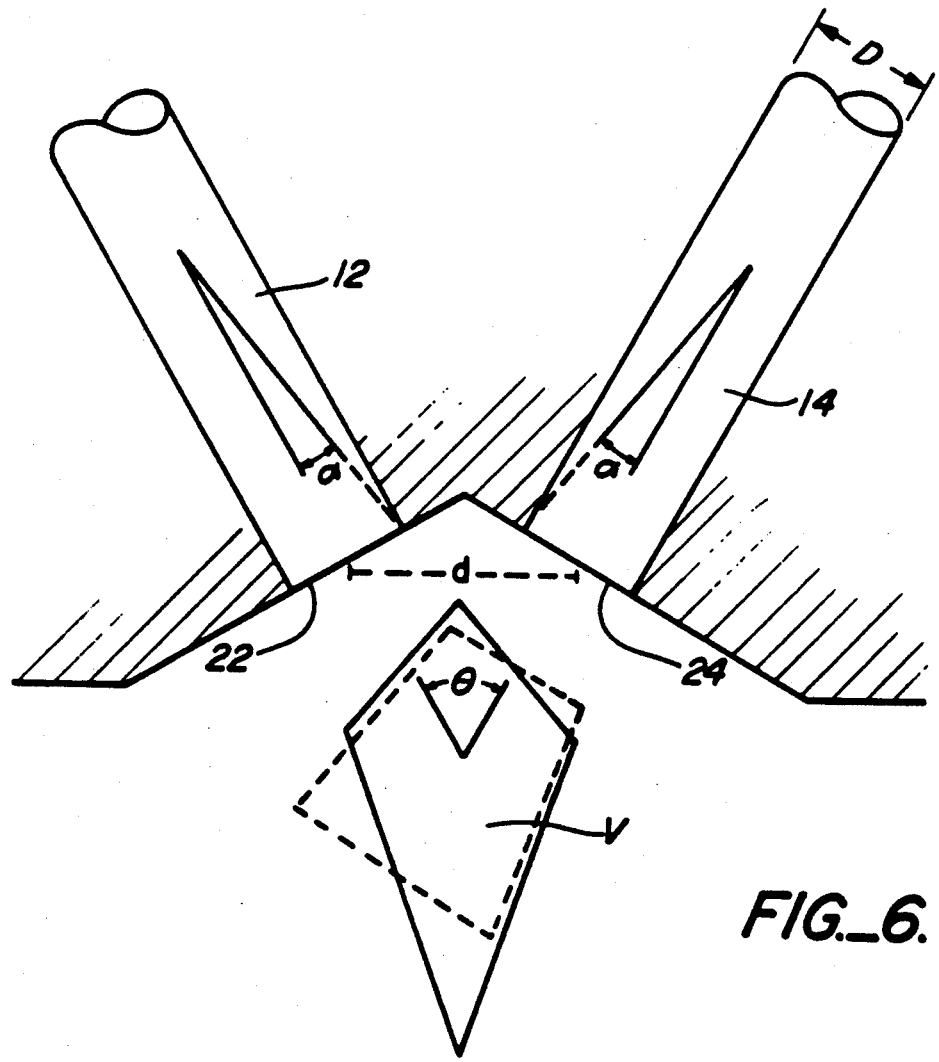
FIG._6.

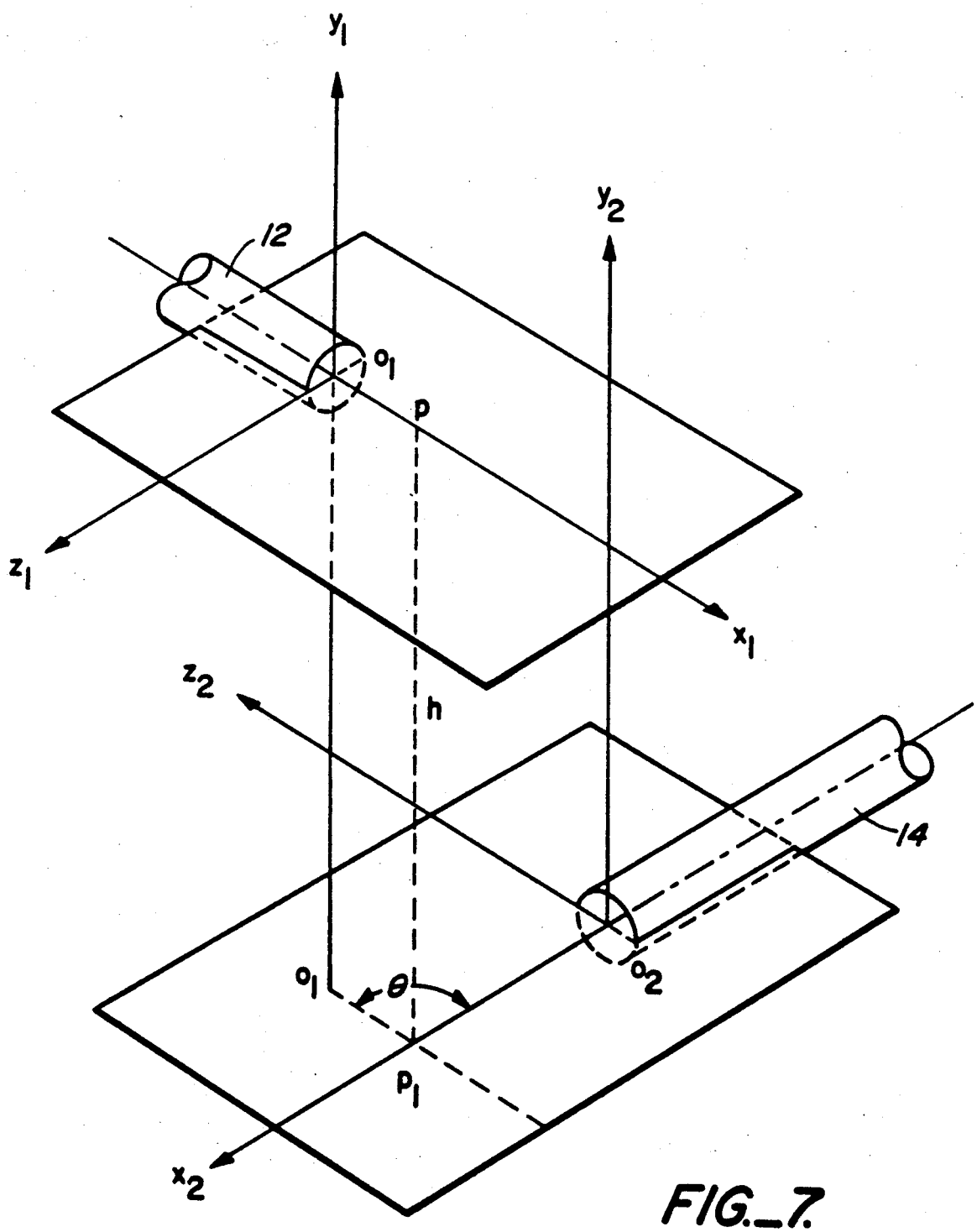
FIG._7.

METHOD FOR DETECTION OF FLUORESCENCE OR LIGHT SCATTER

This is a continuation of pending application Ser. No. 176,475, filed April 1, 1988, incorporated herein by reference, now U.S. Pat. No. 4,934,811.

BACKGROUND OF THE INVENTION

1. Field of the Invention

The present invention relates to an apparatus and method for detecting fluorescence or light scatter, which may relate to the presence or absence of an analyte, in a liquid sample. In particular, the invention relates to a dual optical fiber probe in which the spatial configuration of the optical fibers is arranged to define a finite interrogation volume independent of the volume of the liquid sample. The interrogation volume can be visualized as the intersection of the two light cones emanating from the first and second optical fibers having a determined spatial configuration when each optical fiber transmits visible light. The size of the interrogation volume is determined by the spatial orientation and optical parameters of the dual optical fibers, preferably creating an interrogation volume of less than $10^{-5}$ cubic centimeters. The invention is particularly useful for clinical laboratory applications such as blood typing.

2. State of the Art

Cells and other particles in the range of 0.05 to 100 microns suspended in a liquid medium have been individually detected by streaming the liquid to provide a fine stream or to create very small droplets so as to provide a detection volume and monitoring of the light scattered by the particles, including Rayleigh and Raman light scattering, or that emitted from the particles such as by fluorescence. The basic principle of light scattering from a small volume is used in flow cytometers. Commercial instruments utilizing light scattering and fluorescence for particle detection are available.

PCT patent application Publication No. WO 85/05680, published Dec. 19, 1985, describes an optical system for use in flow cytometers that includes multiple optical fibers disposed about and on an orifice plate used to define the flow stream.

Briggs (U.S. Pat. No. 4,564,598) describes principles for the detection of particles that are not confined to small volumes. As described therein, a small detection volume is achieved by illuminating the bulk suspension with a very narrow beam of light, e.g. 10-100 microns, delivered through an optical fiber immersed in the fluid and collecting the light scattered at the tip of the fiber by allowing it to pass back through the fiber past a beam splitter. Because the same fiber is used for illuminating the particles as well as collecting the emitted light, the method is generally useful only where the emitted light is wavelength shifted as in flourescence. Under these conditions, internal scatter of the fiber can be largely filtered out to permit detection of the signal. However, even when detecting fluorescence, the background scatter limits sensitivity. While in principle multiple wavelengths can be monitored, multiple splitters must be used which further decrease sensitivity and also increase the cost and complexity of the system.

Other devices and apparatus have been described for the detection and measurement of scattered and emitted light from particles. United Kingdom Pat. No. 1,506,017 describes a fluorometric system including two optical fibers that transmit and receive electromagnetic radiation to and from the sample-coated surface of a macrobody (typically a sphere on the order of 5-20 millimeters in diameter). The optical fibers are preferably disposed at a small angle, less than thirty degrees, relative to each other. The fibers are not utilized to define a volume in a liquid sample from which the presence or absence of an event will be monitored.

Japanese patent application No. 84230306, filed Nov. 2, 1984 (Publication No. 61110033, dated May 28, 1986) describes the use of a plurality of optical fibers to measure particle agglutination.

U.S. Pat. No. 4,564,598 (Briggs), noted previously, describes an optical fiber probe having a single optical fiber, that both supplies the incident radiation and receives the excitation signal, to measure fluorescent signals in a fluid sample. U.S. Pat. No. 4,537,861, (Elings et al) describes an immunoassay technique in which labelled, bound ligand-antiligand complexes are caused to reside in a predetermined spatial pattern that then can be scanned to detect a signal level relative to background signal. European patent Publication No. 0175545, published Mar. 26, 1986 (application No. 85306450.9, filed Nov. 11, 1985) describes a method for particle detection that autocorrelates the intensity of an electromagnetic signal over a nonzero interval, the duration of which is short compared to the mean duration of the fluctuations.

Additional documents describing particle detection methods are U.S. Pat. No. 4,421,860 (Elings et al) and U.S. Pat. No. 4,560,881 (Briggs) and references described and listed therein.

SUMMARY OF THE INVENTION

The present invention provides an apparatus and a method of detecting in a liquid an optical event (i.e. an event that can be observed by an optical fiber), such as fluctuations in electromagnetic radiation (e.g. fluorescence or light scatter), resulting, for example, from the presence of optical event-causing elements, such as an analyte (e.g. particle or other source of light scatter or fluorescence) or fluorescent fluctuation due to temperature changes, without flowing or otherwise confining the liquid to a necessarily restricted shape or volume, while at the same time greatly decreasing background scattering and providing a way to simultaneously or sequentially monitor radiation of multiple wavelengths.

The invention is directed to a dual optical fiber probe adapted for immersion into a liquid sample, comprising a first optical fiber adapted to guide incident electromagnetic radiation (e.g. light), and a second optical fiber adapted to receive and guide scattered or emitted electromagnetic radiation (e.g. scattered or fluorescent light) resulting from the incident electromagnetic radiation, wherein the first and second optical fibers are adapted to be optically coupled and define a finite interrogation volume in a liquid sample independent of the total volume of the liquid sample. Preferably, the interrogation volume defined is less than $10^{-5}$ cubic centimeters and most preferably less than $10^{-6}$ cubic centimeters. The interrogation volume is formed by spatially arranging the ends of the two optical fibers at the fiber/liquid interface to form an interrogation volume defined by the intersecting light cones of each of the optical fibers when the fibers are energized. The optical fibers are arranged such that light emanating from the first optical fiber is projected at an angle relative to the second optical fiber so that light from the first optical fiber does not substantially enter the second optical fiber in the absence of an optical event-causing element in the interrogation volume. The central longitudinal axes of the optical fibers typically are disposed to approximately intersect and form at their intersection an included angle ranging from about 40° to 140°, and most preferably being about 60°. In addition to the included angle, the distance between the longitudinal axis of each fiber at the liquid/fiber interface, the degree of coplanarity of the fibers, and the core diameter and numerical aperture of each fiber is selected to determine the desired size of the interrogation volume.

The dual fiber probe of the present invention is particularly advantageous in that reflection at the interface of the optical fiber and liquid is not a factor, and the background due to reflection from a cuvette wall is minimized. Additionally, by appropriate choice of the physical and optical parameters of the optical fibers, i.e. numerical aperture, core diameter and separation distance, as well as the angular positioning, the size of the interrogation volume can be adjusted to systems of interest. Moreover, a scattering signal and a fluorescent signal, or two fluorescent signals, can be detected at the output fiber with the aid of a beam splitter and two sets of filters, a filter wheel with two filters or a demultiplexer.

BRIEF DESCRIPTION OF THE DRAWINGS

FIG. 1 is a schematic of the overall detection apparatus employing the dual fiber optical probe of the present invention;

FIG. 2 is a sectional view of the dual fiber optical probe of the present invention;

FIG. 3 is an end view of the dual fiber optical probe of FIG. 2;

FIG. 4A is a front view of one half of the probe insert for maintaining the optical fibers in a preferred spatial configuration;

FIG. 4B is a side view of the half of the probe insert of FIG. 4A;

FIG. 5A is a front view of the other half of the probe insert for maintaining the optical fibers in a preferred spatial configuration;

FIG. 5B is a side view of the half of the probe insert of FIG. 5A;

FIG. 6 is an illustration of one configuration of the optical fibers of the dual fiber optical probe showing the optical coupling of the fibers and the interrogation volume; and FIG. 7 is an illustration of system geometry when the optical fibers are non-planar.

DETAILED DESCRIPTION OF THE INVENTION

For the purposes of the foregoing and following descriptions, "interrogation volume" means a spatial volume, defined by first and second optical fibers having a determined orientation and physical characteristics, in which an electromagnetic (e.g. optical) event (such as fluorescence or light scattering) resulting from electromagnetic radiation (e.g. light) emanating from one optical fiber will be sensed by the second optical fiber. The interrogation volume can be visualized as the intersection of the two light cones emanating from the first and second optical fibers having a determined spatial configuration when each optical fiber transmits visible light. "Optical coupling" means the circumstance where an optical event (such as fluorescence or light scattering) resulting from electromagnetic radiation (e.g. light) emanating from one optical fiber is sensed by a second optical fiber with the proviso that light emanating from the first optical fiber does not substantially enter the second optical fiber in the absence of an optical event-causing element; the two optical fibers are then considered to be "optically coupled".

With reference to FIGS. 1-5, the dual fiber probe 10 of the present invention utilizes an input optical fiber 12 to transmit electromagnetic radiation (e.g. light) from an electromagnetic radiation source 16, and an output optical fiber 14 to transmit subsequently collected radiation (e.g. scattered or fluorescent light) to a detector 18. Radiation source 16 may be of single wavelength or multiple wavelength, appropriately filtered as required by conventional applications. Wavelengths of between 200-1500 nanometers, prefereably 400-900 nanometers, can be conventionally utilized. Depending on the particular wavelength desired lasers may be utilized, and Helium/Neon lasers have been found suitable. The probe 10 itself consists of an elongated, probe housing 20, generally consisting of a hard, cylindrical sheath 21 (e.g. a stainless steel tube) surrounding a molded, probe insert 40 in which are mounted optical fiber 12 and optical fiber 14. Optical fibers 12 and 14 are conventionally clad (the cladding not being shown) on their external, circumferential surfaces and terminate in end faces 22 and 24, that typically will be highly polished.

The ends of optical fibers 12 and 14 are rigidly held in a spaced, angularly disposed configuration by insert 40. Typically, insert 40 is molded in two substantially semi-cylindrical halves 41 and 49. Conventional molding materials can be utilized.

One insert half 41 is formed with a lower portion 42 that has a groove 45 (preferably V-shaped) formed in its bottom surface and angularly disposed grooves 44 in its face. Grooves 44 are formed in face 42 at an appropriate angle to each other such that the longitudinal axes of optical fibers 12 and 14 intersect at the desired angle when placed therein. The upper portion 43 of insert half 41 is formed with holes 46 and 48 to accomodate mating members on second insert half 49 to facilitate alignment of the insert halves 41 and 49 when they are joined. A cylindrical abutment 47 surrounding hole 48 is provided as a spacer means in the completed insert assembly.

Second insert half 49 is formed with a lower portion 50 having a groove 52 (preferably V-shaped) in its bottom surface. Groove 52 aligns with groove 45 when insert halves 41 and 49 are joined to form a completed insert assembly. Portion 50 is complementary to portion 42 and is positioned immediately adjacent portion 42 in the completed insert assembly 40 to capture fibers 12 and 14 in a determined spatial configuration and provide for a liquid/fiber interface formed within grooves 45 and 52. Upper portion 51 is formed with members 53 and 54 that are adapted to mate with holes 46 and 48, respectively in insert half 41. A flange 55 surrounds member 54 and cooperates with abutment 47 to provide accurate spacing in the completed assembly of insert 40.

During manufacture of the probe 10, faces 22 and 24 of the emission and collection ends, respectively, of optical fibers 12 and 14 are highly polished and the ends are placed within grooves 44 and fastened in place, typically with an ultraviolet-cured epoxy. Thereafter, sheath 21 is placed about the insert and back-filled with epoxy and cured to provide a completed unitary assembly in which the optical fiber faces 22 and 24 are spatially configured in the manner desired.

As part of the overall probe system, input end 30 of optical fiber 12 receives light transmitted through a focusing means 28, as for example provided by a conventional lens or lenses, which itself receives light from light source 16. Optical fiber 12 transmits and guides light to end face 22, and into a liquid sample volume in which the probe is inserted. The resulting light from a particle or solution, which may appear either by scattering or fluorescence within the interrogation volume, is received by output light fiber 14 at end face 24 and transmitted and guided via that optical fiber to output end 38 of fiber 14. The emitted output light conventionally is transmitted through filter means 36 and received within housing detector 32 by a photomultiplier tube 34. Conventional systems (e.g. high gain EMI photomultiplier) can be utilized. Filter means 36 may comprise single or multiple band-pass filters, or various beam splitters, to monitor fluorescent or scattered radiation as appropriate. The signal so generated and received is then processed in accordance with conventional methods.

With reference to FIG. 6, the interrogation volume generally designated V (represented in the drawing in two-dimensions by the solid line) can be visualized as the intersection volume of the respective light cones emanating from the end faces 22 and 24 of optical fibers 12 and 14, respectively, when both the optical fibers are energized (i.e. light is transmitted by both fibers). The size of the interrogation volume is determined from the angle $\phi$ and separation distance d of the longitudinal axes of the input and output optical fibers 12 and 14 at the liquid/fiber interface, as well as the core diameter (D) of each fiber and its numerical aperture (N.A.). With reference to FIG. 6, in general the angle $\theta$ will have to be greater than the sum of the arcsines of the numerical apertures of the two fibers, where the numerical aperture is the sine of the vertex angle $\alpha$ of the largest cone of meridional rays that can enter or leave the fiber end multiplied by the refractive index of the medium in which the vertex of the core is located. If angle $\theta$ is equal or less than this sum, then the outermost rays define a volume that is infinite or undefined. The angle $\theta$, however, must be less than 180° minus the sum of the arsines of the two numerical apertures such that the rays of one fiber cannot enter the other fiber. For a simple case, it can be assumed that the optical fibers have the same optical and physical characteristics, and are located such that the distance of each fiber face from the point of intersection of the longitudinal axes of the two fibers is equal. A reasonable estimate of the interrogtion volume, V, can be given by the following calculation for angles of $\theta$ relatively larger than the sum of the arcsines of the numerical apertures.

$$V = \tfrac{1}{3}\pi \text{TAN}^2(\alpha)(h_2^3 - h_1^3)$$

where $$h_1 = Z\left(1 - \frac{\sin \alpha}{\sin(\theta + \alpha)}\right)$$

$$h_2 = Z\left(1 + \frac{\sin \alpha}{\sin(\theta - \alpha)}\right)$$

and $$Z = \frac{d}{2 \sin \frac{(\theta)}{2}} + \frac{D}{2} \cot \alpha$$

$$\alpha = \text{ARCSIN}(N.A.)$$

where
N.A. = numerical aperture
D = diameter of fiber core
d = distance between longitudinal axes at liquid/fiber interface
$\theta$ = included angle of intersection of longitudinal axes of fibers at liquid/fiber interface.

This approximated interrogation volume is shown in two dimensions by the dashed lines of FIG. 6.

In a presently preferred embodiment, optical fibers 12 and 14 are formed from a 50/125 all-silica step-index fiber having a core diameter of 50 microns; a cladding diameter of 125 microns and a numerical aperture of 0.22. The angle $\theta$ and distance d are preferably 60° and 200 microns, respectively. The 60° orientation presents an interrogation volume that facilitates the detection of a limited number of large, very bright particles in the presence of a large number of smaller, less-bright particles, such as for example will occur in an agglutination assay wherein the aggregates are large and highly fluorescent. Additionally, in a preferred configuration the fibers are substantially coplanar. The interrogation volume defined by the dual fiber probes typically will be less than $10^{-5}$ cubic centimeters, preferably less than $10^{-6}$ cubic centimeters.

The following table illustrates various probe configurations that are suitable. In each instance, the optical fibers are coplanar. The listed volumes of the table are determined from the foregoing formulae. In any instance, the interrogation volume can be measured by passing particles of increasing concentration through the interrogation volume until one particle will always be found in the interrogation volume, as measured by fluctuation analysis or pulse height analysis. The interrogation volume is then the reciprocal of this particle concentration. In general, the smaller the interrogation volume V, the greater the concentration of particles that can be measured.

TABLE 1

| Numerical Aperture | $\theta$ (deg) | Axial Separation (microns) | Core Diameter (microns) | Volume (cm³) |
|---|---|---|---|---|
| .22 | 60 | 150 | 50 | $1.6 \times 10^{-6}$ |
| | 60 | 200 | 50 | $2.8 \times 10^{-6}$ |
| | 60 | 300 | 50 | $6.4 \times 10^{-6}$ |
| | 90 | 150 | 50 | $7.5 \times 10^{-7}$ |
| | 90 | 200 | 50 | $1.2 \times 10^{-6}$ |
| | 90 | 300 | 50 | $2.5 \times 10^{-6}$ |
| .22 | 60 | 150 | 100 | $4.8 \times 10^{-6}$ |
| | 60 | 200 | 100 | $6.9 \times 10^{-6}$ |
| | 60 | 300 | 100 | $1.3 \times 10^{-5}$ |
| | 90 | 150 | 100 | $2.6 \times 10^{-6}$ |
| | 90 | 200 | 100 | $3.5 \times 10^{-6}$ |
| | 90 | 300 | 100 | $6.0 \times 10^{-6}$ |
| .11 | 60 | 150 | 50 | $5.4 \times 10^{-7}$ |
| | 60 | 200 | 50 | $7.8 \times 10^{-7}$ |
| | 60 | 300 | 50 | $1.5 \times 10^{-6}$ |
| | 90 | 150 | 50 | $3.1 \times 10^{-7}$ |
| | 90 | 200 | 50 | $4.2 \times 10^{-7}$ |
| | 90 | 300 | 50 | $7.2 \times 10^{-7}$ |
| .11 | 60 | 150 | 100 | $2.2 \times 10^{-6}$ |
| | 60 | 200 | 100 | $2.8 \times 10^{-6}$ |
| | 60 | 300 | 100 | $4.3 \times 10^{-6}$ |
| | 90 | 150 | 100 | $1.5 \times 10^{-6}$ |
| | 90 | 200 | 100 | $1.8 \times 10^{-6}$ |

TABLE 1-continued

| Numerical Aperture | θ (deg) | Axial Separation (microns) | Core Diameter (microns) | Volume (cm$^3$) |
|---|---|---|---|---|
|  | 90 | 300 | 100 | $2.5 \times 10^{-6}$ |
| .11 | 50 | 50 | 10 | $2.4 \times 10^{-8}$ |
|  | 40 | 500 | 10 | $6.7 \times 10^{-6}$ |
|  | 40 | 1000 | 10 | $4.9 \times 10^{-5}$ |
|  | 140 | 50 | 10 | $4.8 \times 10^{-9}$ |
|  | 140 | 500 | 10 | $3.9 \times 10^{-7}$ |
|  | 140 | 1000 | 10 | $2.5 \times 10^{-6}$ |
| .11 | 40 | 50 | 200 | $1.3 \times 10^{-5}$ |
|  | 40 | 500 | 200 | $6.2 \times 10^{-5}$ |
|  | 40 | 1000 | 200 | $1.9 \times 10^{-4}$ |
|  | 140 | 50 | 200 | $1.0 \times 10^{-5}$ |
|  | 140 | 500 | 200 | $2.1 \times 10^{-5}$ |
|  | 140 | 1000 | 200 | $3.8 \times 10^{-5}$ |
| .7 | 90 | 50 | 10 | $5.2 \times 10^{-7}$ |
|  | 90 | 500 | 10 | $3.6 \times 10^{-4}$ |
|  | 90 | 1000 | 10 | $2.8 \times 10^{-3}$ |
| .7 | 90 | 50 | 200 | $2.0 \times 10^{-5}$ |
|  | 90 | 500 | 200 | $7.4 \times 10^{-4}$ |
|  | 90 | 1000 | 200 | $4.1 \times 10^{-3}$ |

With reference to FIG. 7, the spatial relationships of the fiber ends 22 and 24 located in probe 20 can be defined by constructing a pair of parallel planes passing through each fiber end and longitudinal axis where the planes are separated by a distance h, the dihedral angle between the fibers (defined by the angle $O_1'P'O_2$ between the plane described by lines $O_1P$ and $PP'$ and the plane described by line $O_2P'$ and $PP'$) is θ. When the ends of the optical fibers are coplanar (i.e. h=0), the dihedral angle becomes the included angle between the intersecting longitudinal axes of the fibers. In the description herein, it will generally be assumed that the fiber ends are substantially coplanar so that the dihedral angle and included angle are substantially the same. In general, the minimum θ that will provide a finite overlap volume will be greater than arcsin A plus arcsin B where A and B are the numerical apertures of the two fibers. Preferably h=0 and θ=40°-140°, preferably 40°-120°, more preferably 40°-80°, usually about 60°.

When h=0, it is preferable for the distances $O_1P$ and $O_2P'$ to be as small as possible by causing the optical fibers to nearly contact each other. Higher values of the distances $O_1P$ and $O_2P'$ are acceptable provided the overlapping volume criterion is met. When h ≠ 0, the cones will not overlap optimally and thus the intensity of light projected from one fiber that is scattered will be suboptimally collected by the other fiber. Balancing the disadvantage of this reduction in sensitivity is the opportunity provided by this configuration for greater flexibility in selecting the size of the overlapping volume. Thus, as h is increased, the overlapping volume of the intersecting cones can be decreased to any desired value. Obviously, h must not be so large that this volume is reduced to zero. In practice, a compromise will be made between reducing the volume on the one hand and loss of signal intensity as a result of reduction of light collection on the other hand. Moreover, when small volumes are defined by increasing h, the volume will become exceptionally sensitive to the acceptance angle of the fibers. Since the latter varies with refractive index of the fluid, a probe constructed in this way could become overly sensitive to refractive index.

The values of $O_1P$ and $O_2P'$ likewise are dictated by practical considerations such as the ease and reproducibility of probe assembly and light collection efficiency. In general, as $O_1P$ and $O_2P'$ increase, the overlapping volume increases. Selection of minimum values for $O_1P$ and $O_2P'$ will therefore be preferred.

The core diameters of the fibers, that is the portion of each fiber carrying the light, will be the range of 10-200 microns, preferably 25-75 microns. The core diameters may be the same or different, most preferably the same, and it will usually be desirable to minimize the acceptance angle rather than core diameter in order to reduce the overlap volume without loss of light collection efficiency. When the core sizes are different, it will be preferable that the core of the excitation light fiber be smaller. Numerical apertures in air of the optical fibers of 0.09-0.7 can be used. In the type of applications described herein, numerical apertures of 0.11-0.24 can be used, with 0.22 being preferable. The angle θ can be between about 40 to 140 degrees. For clinical applications, 40-80 degrees is suitable, 55-65 degrees more typical and 60 degrees is preferred. Angles of 90° or greater are suitable for simply counting fluorescent particles or creating a more homogeneous interrogation volume in which any fluorescent particle will be detected. The separation distance between the longitudinal axes of the optical fibers at the fiber/liquid interface typically is in the range of about 0.05-1.00 millimeters, preferably 0.2 millimeters.

In general, probes of this invention are used by illuminating one optical fiber at the end distal to the probe with the illuminating light and monitoring scattered or fluorescent light collected by the proximal or probe end of the second optical fiber with a photodetector at the distal end of the optical second fiber. For detection of particles, the probe assembly is immersed in a sample of the fluid to be analyzed and moved relative to the fluid to provide for sequential interrogation of multiple small volumes defined by the interrogation volume. In this way detection of light scattering produced internally in the illuminating fiber 12 is largely excluded from detection, the background signal is correspondingly reduced, and the sensitivity thereby increased. Detection of particles either by conventional light scattering or fluorescence can be carried out by monitoring the fluctuations of the scattered or emitted light, as for example by conventional pulse height analysis or time correlation methods.

In certain cases, it will be desirable to measure both fluorescence and Raleigh light scattering from the same sample. Where it is sufficient for this to be done sequentially, the above described system can be used. Where simultaneous measurement is required, the Raleigh scatter can be measured at the distal end of output fiber 14 and the fluorescence can be measured by collecting the scattered light passing back up input fiber 12 by use of a splitter. For example, one could use means such as described in U.S. Pat. No. 4,564,598 which is incorporated herein by reference. Other conventional methods could be used as well.

When the apparatus described is utilized to irradiate a receiver suspected of containing an event causing element (e.g. analyte), the signal resulting from the irradiation of such an element can be detected and measured in an enhanced manner relative to the background radiation. The selected element can comprise diverse entities depending on the measurement system in question. For example, the element can be a particle which fluoresces or elastically scatters light in response to incident radiation. It may be a particle which absorbs incident radiation such that the presence of the particle is detected by a negative fluctuation from a base value for the overall electromagnetic signal emitted. As a further example, the element or object may be an entity having a characteristic causing it to emit a greater signal than the same entity not having the particular characteristic (e.g. a cell having an abnormality which causes it to emit a larger or more powerful signal than that same cell not having the abnormality).

The subject invention has particular application for determining an analyte in a sample, where the amount of analyte affects an observed pattern of fluorescence fluctuations. The analyte is a member of a specific binding pair consisting of ligand and its homologous receptor. The input and output optical fibers are employed to irradiate a portion of the sample volume and to receive fluorescent light from the sample volume, respectively. One observes a plurality of such volumes, either by observing a single volume over an extended period of time, where particles move in and out of the volume, or scanning a plurality of volumes either simultaneously or successively, or combinations thereof. Thus, the percentage of volumes observed which have a predetermined difference in fluorescence from a defined level can be related to the amount of analyte in the medium.

The fluctuations in fluorescence can be achieved by various combinations of particles and continuous media. For example, the combinations can include particles which fluoresce at constant intensity in a non-fluorescing solution, particles which fluoresce at varying intensity in a non-fluorescing solution, particles which are non-fluorescent in a fluorescent solution and fluorescent particles in a fluorescent solution. Furthermore, the fluorescent fluctuation may be a result of aggregation of particles, non-fluorescent particles becoming fluorescent, or fluorescent particles becoming non-fluorescent. The particles may be comprised of polymers, both naturally occurring or synthetic, natural particles, such as virions and cells, e.g., blood cells and bacteria, or the like. Particle sizes will vary from 0.05 to 100 microns, where synthetic particles will generally be from about 0.1 microns to 10 microns diameter.

By employing the above-described method in a fluorescent assay, a large number of protocols and reagents may be employed. One group of protocols will involve measuring fluorescent particles. This group can be further divided into particles which remain uniformly fluorescent, that is, there are basically two particle populations, fluorescent or non-fluorescent, where fluorescence above a certain level is defined as a positive or negative result. The invention has been found to be particularly advantageous in protocols in which a fluorescing molecule is conjugated directly to an antibody (Ab), which then binds directly to a cell.

A heterogeneous population of fluorescent particles can come about in a number of ways. For example, one can have aggregation or agglutination of particles. The analyte could be a receptor or antibody, which is polyvalent in binding sites. Fluorescent particles could be conjugated with ligand, so that the polyvalent receptor would act as a bridge between particles. In this way, the greater the amount of analyte present in the medium, the larger the number of aggregates which will result. The particle of interest could then be chosen as a particle which is an aggregation of two or more or three or more particles. Furthermore, by appropriate electronic means, one could determine the size of the aggregation, counting not only the total number of particles, but the number of members of each population. As the aggregation increases in size, the fluorescence of the aggregate particle will also increase, but not linearly with the increase in the number of particles in the aggregation.

In a second way for having a heterogeneous population, one could have a non-fluorescent particle, where fluorescent molecules become bound to the particle in proportion to the amount of analyte in the medium or to the number of binding sites on the particle. For example, one could have fluorescent molecules bound to an antiligand. Ligand could be bound to a non-fluorescent particle. The fluorescer conjugated antiligand would be combined with the analyte containing sample, so that the analyte could fill the binding sites of the antiligand, with the remaining binding sites being related to the amount of analyte in the sample. Upon addition of the ligand conjugated particles to the medium, the remaining fluorescent conjugated receptor would bind to the particles, providing for a distribution of particles of varying fluorescence.

A third technique may also be illustrated by employing an aggregation. In this technique, non-fluorescent particles are employed, and the continuous phase is made fluorescent. Thus, when the aggregation is present in the sample volume, there will be a substantial diminution in the observed fluorescence. These particles, while non-fluorescent should also be substantially opaque to excitation of fluorescent light. Thus, they will create a substantial shadow, inhibiting the detection of fluorescence in a volume substantially greater than the volume of the aggregation.

A fourth way of obtaining a heterogeneous population of fluorescent particles is to allow a fluorescent tag to label non-fluorescent particles. For example, non-fluorescent particles may be cells which have a plurality of antigens on the cell surface, there being a number of each antigen present. By employing fluorescer-labeled-antibodies to specific surface antigens, a specific set of non-fluorescent cells will become fluorescent. The detection of the presence of such cells is a method of cell identification, e.g. red blood cell (RBC) grouping and typing. For example, in the A, B, O system, if the fluorescent tag were conjugated to anti-A antibody, binding would occur and there would be a greater increase in cell fluorescence if the sample contained the A antigen of type A or type AB blood than if the analyte contained blood types B or O. Alternatively, cells can also be labeled by employing a fluorescent cell-incorporative dye such as those described in European Patent Publication No. 176,252, published Apr. 2, 1986, which is incorporated herein by reference.

In addition to antibodies, certain lectins are known to bind in varying degrees to RBC surface antigens, and are convenient receptors for use in fluorometric assays.

Usually, there will be a distribution of levels of fluorescence, although in some situations it will be feasible to substantially saturate the available binding sites on the cell surface, so as to approximate only two populations, non-fluorescent cells and cells of substantially uniform fluorescence.

While not presently preferred, typing red blood cells (RBCs) or identifying red blood cell (RBC) antigens or the antibodies thereto can be effective by using the RBCs as fluorescence quenchers in an assay employing fluorescent particles to provide a detectable signal. Substances which bind to RBC antigens, normally antibodies or lectins (hereinafter "receptors") are conjugated to fluorescent particles. A solution of particle-conjugates is combined with red blood cells, e.g., whole blood, with an appropriate buffer. If an antigen is present on the RBCs that has a binding or determinate site specific for the receptor, the conjugated particles will bind to the RBCs which act as fluorescence quenchers.

Also, the determination of the presence of antibodies to a RBC antigen can be made. Three different techniques may be used. In one, fluorescently labeled antibody compete with antibodies in the plasma or serum sample for antigen sites on test RBCs of a known group, with the observed cellular fluorescence decreasing with increasing amounts of antibodies against the specific antigen in the sample. Alternatively, the test RBCs may be fluorescently stained and, when combined with serum, the specific antibodies, if present, will agglutinate the fluorescent cells. In a third method, the fluorescent bead may be conjugated with the surface antigen of interest and antibodies present in the sample act as a bridge between RBCs of known type and the antigen conjugated fluorescent particles. In this situation, decreasing fluorescence would indicate the presence of the antibodies.

High extinction coefficients for the fluorescer are desirable and should be greatly in excess of 10,000 $cm^{-1} M^{-1}$ and preferably in excess of 100,000 $cm^{-1} M^{-1}$. The fluorescer should also have a high quantum yield, preferably between 0.3 and 1.0.

In addition, it is desirable that the fluorescer have a large Stokes shift, preferably greater than 20 nm, more preferably greater than 30 nm. That is, it is preferred that the fluorescer have a substantial spread or difference in wavelengths between the absorption and emission maxima.

One group of fluorescers having a number of the desirable properties are the xanthene dyes, which include the fluoresceins derived from 3,6-dihydroxy-9-phenylxanthhydrol and rosamines and rhodamines, derived from 3,6-diamino-9-phenylxanthene. The rhodamines and fluoresceins have a 9-O-carboxyphenyl group, and are derivatives of 9-O-carboxy-phenylxanthene.

These compounds are commercially available with or without substituents on the phenyl group.

Another group of fluorescent compounds are the naphthylamines, having an amino group in the alpha or beta position, usually alpha position. Included among the naphthylamino compounds are
1-dimethylaminonaphthyl-5-sulfonate,
1-anilino-8-naphthalene sulfonate and
2-p-toluidinyl-6-naphthalene sulfonate.
Other fluorescers of interest include coumarins, e.g., umbelliferone, and rare earth chelates, e.g., Tb, Eu, etc. Descriptions of fluorescers can be found in Brand, et al., *Ann. Rev. Biochem.*, 41, 843–868 (1972) and Stryer, *Science*, 162, 526 (1968). Still another group of fluorescers are the squarate dyes described in Euopean Patent Publication No. 176,252 noted previously.

Appropriate particles are combined with the fluorescer using standard techniques to provide fluorescent beads or microspheres. Fluorescent particles are commercially available. The fluorescent beads may be varied widely as to size and composition. The beads will normally be made of an inert material and include a plurality of fluorescent chromophoric functionalities. The beads will have a sufficient concentration of fluorescent functionalities to provide for a large signal per bead. Various organic polymers may be employed for the bead, e.g., polystryrene, polymethacrylate or the like or inorganic polymers, e.g., glass or combinations thereof. The particular choice of the polymeric composition is primarily one of convenience.

Conjugated to the fluorescent beads either covalently or non-covalently are receptors which may be antibodies, including monoclonal antibodies, or lectins, that bind either specifically or differentially to specific RBC surface antigens or antigens having the determinant site(s) of such RBC surface antigens or other antigens of interest.

The receptors are absorbed to the fluorescent bead using standard techniques extensively described in the literature. Alternatively, the receptors may be covalently bound by conventional techniques.

The sequential or simultaneous measurement of scattered and fluorescent light in conjunction with the present apparatus permits a particularly facile method of detecting the presence of an analyte suspected of being in a fluid sample by detecting a first event (e.g. agglutination) associated with the presence of the analyte and a second event (e.g. absence of agglutination) associated with an interfering element that potentially can interfer with the detection of the first event. Other applications include cell differentiation, (such as with double fluorescent labeled cells) aerosol detection and measurement, tracer flow controls, and the like, wherein a multitude of exiting wavelengths is utilized by beam splitting or use of a multitude of output fibers.

The present invention contemplates equivalent multifiber probes, e.g. tri-fiber optic probe having three optical fibers, wherein the third optical fiber is introduced at the apex of the V-groove of the dual fiber probe, such that all three fibers have a common interrogation volume. The tri-fiber probe could be used in the manner described herein with two detector units, each having a filter for specified wavelengths, associated with two of the optical fibers and the light source associated with the third optical fiber.

The dual fiber probe of the present invention is useful in a method of determining the presence or absence of an analyte that involves adding a fluorescently tagged receptor for an analyte to a fluid sample that is suspected of containing the analyte and possibly an interfering substance. Next, the combined sample/receptor is processed to remove the suspected interfering substance, such as by washing or the like. Then the processed sample/receptor is treated with an event actuator (e.g. an agglutination reagent) and irradiated. The fluorescent signal at the emitted wavelength and the scattered signal at the incident wavelength are measured and compared to their respective background values. With analyte positive samples in the absence of an interfering substance, either originally absent or effectively removed by processing of the sample, an increase in the fluorescent particle signal heights from background indicates the presence of the analyte. Analyte negative samples are evidenced by fluorescent particle heights substantially the same as background and increased light scattering particle signal heights relative to background. Improperly processed samples (i.e. those in which the interfering substance has not been effectively removed) are evidenced by the absence of fluorescent particle signal heights in excess of background and a suppression of light scatter particle signal heights relative to background.

In the following examples, the dual fiber probe is formed in the manner described herein from 50/125 all silica step-index fiber having a core diameter of 50 microns; a cladding diameter of 125 microns and a numerical aperture of 0.22. The angle $\theta$ and distance d are 60° and 200 microns, respectively, and the fibers are coplanar.

EXAMPLE 1

The dual fiber probe is employed in a method for screening for antibodies in a patient's blood. In this method, test cells bearing various surface antigens are stained with fluorescent dye. After mixing with the patient's plasma, the test cells are thoroughly washed and combined with anti-human immunoglobulin antiserum. Typically, when antibodies are present, this reagent will agglutinate the test cells. The present device premits detection of the agglutinated cells with the dual fiber probe while illuminating with 633 nm light. Using a particle signal height discriminator (i.e. event height discriminator), the magnitude of the light pulses detected by the photodector at the distal end of the second fiber signals an agglutination event.

Failure to properly wash the test cells can lead to residual immunoglobulins in the solution that may block the agglutination by the anti-human immunoglobulins. The present device makes it possible to provide a control to assure that the test cells are properly washed. For this purpose, unstained check cells that were coated with human IgG were added to the washed test cells. Only if washing of the test cells is complete will anti-human immunoglobulin aggregate the check cells.

The assay was carried out by first monitoring the fluorescence particle signal heights using a filter between the second fiber and the photodetector to remove 633 nm excitation light. The filter was then changed to a 633 nm band pass filter in order to monitor 633 nm pulses from light scattered by agglutinated check cells. With antibody positive samples, increased fluorescent particle signal heights showed that there was test cell agglutination.

With antibody negative samples, no fluorescent pulses in excess of background were observed showing that agglutination did not occur. Confirmation that the failure of the test cells to agglutinate was not due to poor washing was shown by the ocurrence of increased light scattering particle signal heights in excess of background at 633 nm. Deliberate failure to properly wash led to a suppression of the light scatter particle signal heights relative to background level.

EXAMPLE 2

The sensitivity of the dual fiber probe is demonstrated by measurement of the fluorescent response to various solutions of fluorescent dye, 2-(p-diethylamino-m-hydroxyphenyl)-4-(4-diethylimmonio-2-hydroxy-2,5-cyclo-hexadienylidene)-3-oxo-1-cyclobutenolate (DEAS), in $10^{-3}$M $\beta$ cyclodextrin:

| Average Fluorescence | Dye Concentration (M) |
|---|---|
| 13 | $2 \times 10^{-9}$ |
| 24 | $4 \times 10^{-9}$ |
| 33 | $5 \times 10^{-9}$ |
| 46 | $7 \times 10^{-9}$ |
| 59 | $9 \times 10^{-9}$ |
| 65 | $1 \times 10^{-8}$ |
| 151 | $2.5 \times 10^{-8}$ |
| 180 | $3 \times 10^{-8}$ |
| 227 | $4 \times 10^{-8}$ |
| 281 | $5.5 \times 10^{-8}$ |
| 329 | $7 \times 10^{-8}$ |

Fluorescent response is shown to increase with increasing dye level.

EXAMPLE 3

The following example illustrates the application of the dual fiber probe of this invention for detecting different populations of fluorescing objects (i.e. particles). A population of small latex beads (0.71 microns) were dyed with a squaraine dye (DEAS) at 1×fluorescence and a population of larger latex beads (1.1 micron) were dyed in a similar manner to provide a bead of 4×fluorescence (i.e. the fluorescence of the larger beads are approximately four times that of the smaller beads).

A peak height detector was utilized to determine a sample distribution of number of events versus fluorescence at peak height. That distribution was analyzed to provide an index (i.e. agglutination index) that is the sum of the number of events in each fluorescence level times the difference in fluorescence between that level and the fluorescence cutoff level (set at a multiple of the average fluorescence [av] of the distribution). Differences in the agglutination index at any cutoff indicate an increased fluorescence level due to the presence of the larger bead.

Representative results are shown below:

| | Composition 1: Isotonic buffer containing 0.71 micron dyed latex bead at 2.5 × $10^6$ beads/ml | |
|---|---|---|
| | Agglutination Index | |
| Cutoff | Run 1 | Run 2 |
| av* 1.7 | 880 | 771 |
| av* 1.9 | 338 | 273 |
| av* 2.0 | 208 | 153 |
| av* 2.1 | 208 | 153 |
| av* 2.2 | 125 | 86 |

| | Composition 2: Isotonic buffer containing 0.71 micron dyed latex bead at 2.4 × $10^6$ beads/ml and 1.1 micron dyed latex bead at 0.15 × $10^6$ beads/ml | |
|---|---|---|
| | Agglutination Index | |
| Cutoff | Run 1 | Run 2 |
| av* 1.7 | 2012 | 2145 |
| av* 1.9 | 1221 | 1368 |
| av* 2.0 | 950 | 1095 |
| av* 2.1 | 950 | 1095 |
| av* 2.2 | 739 | 885 |

The greater agglutination index of Composition 2 as compared to that of Composition 1 illustrates the detection of the larger beads.

EXAMPLE 4

The dual fiber probe and the method described in Example 3 was utilized with the following protocols to illustrate the use of the dual fiber probe in blood typing applications.

The protocols for the various assays are as follows:
Protocol I: α A, α B, Forward Control 10 μl of dyed whole blood (50 μM DEAS; 95% DMSO, 5% H₂O) is mixed with 10 μl of Reagent (Anti-A: 149 mg/ml Celltech cell line 3D3 in buffered saline; Anti-B: 110 mg/ml Celltech cell line NB1 in buffered saline) for about 2½ minutes, then diluted with 500 μl of buffered saline solution. The fluorescence of the resulting solution is read in the manner described in Example 3.

Protocol II: A₁ cells, B cells

50 μl of undyed whole blood is mixed with 10 μl of dyed (tetrabutyl squarate: $110^{-4}$ μM is dimethylacetamide, 75 μl per ml of 30% red cell suspension in buffered saline, 2% Pluronics environment) A₁ or B cells, as the case may be, and mixed for about 2½ minutes, then diluted with 50 μl of buffered saline. The fluorescence of the resulting solution is read in the manner described in Example 3.

Protocol III: Rh, Rh control

10 μl of dyed (DEAS) whole blood is mixed with 10 μl of Reagent (Rh: 0.9 mg/ml IgG [reduced and alkylated], 2% PVP, 2% BSA in tris buffer; Rh control: same excluding IgG) for about 2½ minutes, then diluted with about 100 μl of buffered saline. After about 40 seconds of additional mixing, 450 μl of isotonic buffered saline is added and the resulting solution is read in the manner described in Example 3.

The results for A negative and B positive samples are summarized below with cutoffs determined for α A, α B and Forward Control at 1.7 times the average fluorescence, for A₁ cells and B cells at 2 times the average Fluorescence and for Rh, Rh control at 1.8 times the average fluorescence.

|  | αA | αB | Forward Control | A₁ Cell | B Cell | Rh Control | Rh |
| --- | --- | --- | --- | --- | --- | --- | --- |
| A negative | 5867 | 0 | 0 | 0 | 12158 | 0 | 14 |
| B positive | 15 | 12296 | 140 | 11248 | 15 | 7 | 11908 |

While the foregoing invention has been described with reference to the drawings, the Examples and the presently preferred embodiments, they are intended to be illustrative and not to limit the scope of the invention herein claimed. Various modifications or changes to the methods and apparatus described herein will be apparent to those skilled in the art and are intended to be included and encompassed by the claims appended hereto.

What is claimed is:

1. In an assay for the determination of an analyte in a liquid sample by means of at least two angularly disposed optical fibers, the improvement comprising defining a finite interrogation volume of less than about $10^{-5}$ cubic centimeters within said sample with said optical fibers having longitudinal axes by orienting said longitudinal axes so as to intersect with a dihedral angle of between about 40°–140°, immersing said optical fibers within said liquid sample and optically coupling said optical fibers.

* * * * *